United States Patent [19]

Showell et al.

[11] Patent Number: 5,106,853
[45] Date of Patent: Apr. 21, 1992

[54] OXADIAZOLE AND ITS SALTS, THEIR USE IN TREATING DEMENTIA

[75] Inventors: Graham A. Showell, Welwyn Garden City; Leslie J. Street, Harlow, both of England

[73] Assignee: Merck Sharp & Dohme, Ltd., Hertfordshire, England

[21] Appl. No.: 520,891

[22] Filed: May 9, 1990

[30] Foreign Application Priority Data

May 15, 1989 [GB] United Kingdom ................. 8911079
Oct. 12, 1989 [GB] United Kingdom ................. 8923015

[51] Int. Cl.$^5$ .................... C07D 221/02; A61K 31/44
[52] U.S. Cl. ..................................... 514/299; 546/112
[58] Field of Search ................ 548/143, 131; 514/364, 514/299; 546/112

[56] References Cited

FOREIGN PATENT DOCUMENTS

| | | | |
|---|---|---|---|
| 0239309 | 9/1987 | European Pat. Off. | 546/112 |
| 307140 | 9/1988 | European Pat. Off. | 546/112 |
| 307142 | 9/1988 | European Pat. Off. | 546/112 |
| 0323864 | 12/1989 | European Pat. Off. | 546/112 |

Primary Examiner—Mary C. Lee
Assistant Examiner—Robert C. Whittenbaugh
Attorney, Agent, or Firm—Manfred Polk; Charles M. Caruso

[57] ABSTRACT

The compound (3R, 4R)-3-(3-cyclopropyl-1,2,4-oxadiazol-5-yl)-1-azabicyclo[2.2.1]heptane and its salts behave as a functionally selective muscarinic agonist and are useful in the treatment of neurological and mental disorders, preferably in a pharmaceutical formulation comprising the active compound in association with a pharmaceutically acceptable carrier. The compound can be prepared by methods analogous to those known in the art via suitable chiral intermediates and cyclopropyl carboxamide oxime.

5 Claims, No Drawings

OXADIAZOLE AND ITS SALTS, THEIR USE IN TREATING DEMENTIA

The present invention relates to a substituted oxadiazole compound which stimulates central muscarinic acetylcholine receptors and therefore is useful in the treatment of neurological and mental illnesses whose clinical manifestations are due to cholinergic deficiency. Such diseases include presenile and senile dementia (also known as Alzheimer's disease and senile dementia of the Alzheimer type respectively), Huntington's chorea, tardive dyskinesia, hyperkinesia, mania and Tourette Syndrome. Alzheimer's disease, the most common dementing illness, is a slowly progressive neurological disorder characterised by marked deficits in cognitive functions including memory, attention, language and visual perception capabilities.

Published European Patent Applications Nos. 239309 and 323864 disclose a class of oxadiazole compounds which are useful in the treatment of neurodegenerative disorders. It has now been found that a specific isomer of a certain oxadiazole compound is of low intrinsic efficacy (as demonstrated by the NMS/OXO-M ratio) and, as a result, behaves as a functionally selective muscarinic agonist. This results in the compound being a partial agonist at the $M_1$ receptor in the rat ganglion, but as an antagonist at the $M_2$ receptor in the guinea pig heart and at the $M_3$ receptor in guinea pig ileum.

Accordingly, the present invention provides (3R, 4R)-3-(3-cyclopropyl-1,2,4-oxadiazol-5-yl)-1-azabicyclo[2.2.1]heptane and salts thereof (hereinafter collectively referred to as "compound (I)").

Compound (I) may be prepared by methods analogous to those described in, for example, the European patent specifications mentioned above by reacting the corresponding optically active enantiomer of formula (A) or (B) with cyclopropyl carboxamide oxime or a salt thereof

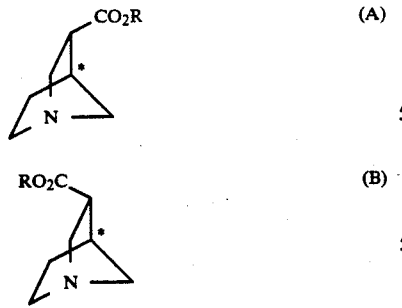

wherein —COOR is —COOH or a reactive derivative thereof (eg. R is H, $C_{1-4}$ alkyl or benzyl) and then separating the exo-oxadiazole product from the corresponding endodiastereomer. The enantiomer of formula (A) or (B) may be prepared by the method of or by a method analogous to those described in the following scheme 1 and description, further details of which can be found in British patent application No. 8911080 which is incorporated herein by reference.

SCHEME FOR PREPARATION OF (B) - SCHEME 1

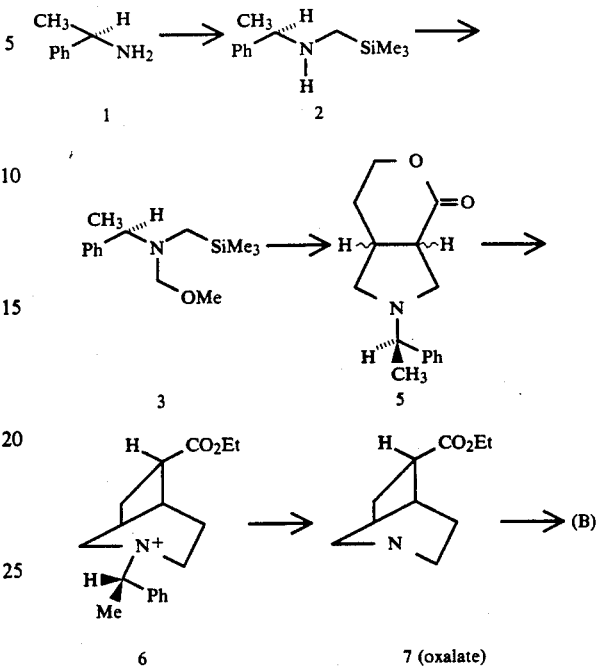

DESCRIPTION

N-((1R)-Phenethyl)-N-trimethylsilyl methylamine (2)

Chloromethyltrimethylsilane (89.9 g, 0.73 mol) was added to R-(+)-α-methylbenzylamine (1, 200.5 g, 1.65 mol, ≧98% optically pure as assessed by chiral GC) and the solution was heated to reflux (~100° C.) with stirring under a nitrogen atomosphere. Heating was continued and over approximately 2 hr the internal temperature rose to 200° C. After a further 2 h at 200° C., the mixture was cooled to 10° C. and the semi-solid mass basified by slow addition of 15% aqueous KOH solution (700 ml). The organic layer was collected and the aqueous was extracted with toluene (2×250 ml). The combined organics were dried ($Na_2SO_4$), evaporated in vacuo and the residual oil was distilled under vacuum. After a fore-run of R-(+)-α- methylbenzylamine (88.2 g; b.p. 75°-85° C. (4 mmHg)) the required aminosilane distilled over (b.p. 82°-84° C. (0.3 mmHg)); (Found: C, 69.62; H, 10.15; N, 6.57. $C_{12}H_{21}NSi$ requires C, 69.49; H, 10.21; N, 6.76%). $^1H$ NMR (360 MHz, $CDCl_3$) 0.0 (9H, s, $Si(CH_3)_3$), 1.31 (3H, d, J=7Hz, Ph-C-$CH_3$), 1.84 and 1.91 (each 1H, each d, J=13.5Hz, $CH_2Si$), 3.63 (1H, q, J=7Hz Ph-$CH$) and 7.17–7.35 (5H, m, $C_6H_5$).

N-Methoxymethyl-N-((1R)-phenethyl)trimethylsilylmethylamine (3)

To an ice-cooled solution of MeOH (17 ml, 0.42 mol) and aqueous formaldehyde (38% solution, 33.2 ml, 0.42 mol) was added the foregoing amino-silane (2, 73 g 0.35 mol) dropwise over 45 min with vigorous stirring. The mixture was allowed to warm to room temperature and then stirred for 4 h. Powdered $K_2CO_3$ (14.1 g, 0.10 mol) was added and the mixture stirred for a further 0.5 h. The layers were separated and the organic layer dried ($Na_2SO_4$), then filtered. The residual inorganic solids were washed with $Et_2O$ (100 ml) and the etherial extracts were combined with the organic material above. Evaporation in vacuo afforded the title compound as a colourless oil which was approximately 80% pure by NMR and used as such within 24 h.

5,6-Dihydro-2H-pyran-2-one (4)

To a suspension of vinyl acetic acid (194.2 g, 2.3 mol) and paraformaldehyde (144.2 g, 4.8 mol) in glacial acetic acid (500 ml) was added conc. sulphuric acid (13 ml). The mixture was heated under reflux for 3 h, cooled to room temperature, then anhydrous sodium acetate (70.5 g) was added with shaking. The acetic acid was distilled off in vacuo, water (400 ml) added and the mixture cooled to 10° C. The mixture was basified to pH=8 by the dropwise addition of 20% sodium hydroxide solution. The aqueous was filtered, extracted with dichloromethane (4×500 ml) and the combined organics washed with saturated sodium chloride solution (500 ml), dried ($Na_2SO_4$), filtered, then evaporated to dryness to give a yellow oil which was distilled under vacuum to give the product as a colourless oil (b.p. 98° C. (7 mmHg)).

2-((1R)-Phenethyl)-4-oxo-1,2,3,6,7,7a-hexahydropyrano[3,4-c]pyrrole (5)

A 1M solution of trifluoroacetic acid (39 ml, 0.039 mol) in $CH_2Cl_2$ was added to a cooled (10° C.) solution of 5,6-dihydro-2H-pyran-2-one (4, 55 g, 0.56 mol), in $CH_2Cl_2$ (400 ml). N-methoxymethyl-N-((1R)-phenethyl)-trimethylsilylmethylamine (122 g, ~0.39 mol) was added dropwise over 45 min. with stirring, during which time an exotherm occurred to 45° C. After addition, the reaction temperature dropped to below 40° C. and the cooling bath was removed. The solution was stirred for a further 2 h, washed with saturated $NaHCO_3$ solution (300 ml) and then with $H_2O$ (300 ml), dried ($Na_2SO_4$) and evaporated in vacuo to give a yellow oil (120.5 g) which was purified by column chromatography on silica (Kieselgel 60, 0.04–0.063 mm, 1.3 kg) using EtOAc-petroleum ether (b.p. 60°–80° C.) (1:1) in order to remove impurities, then EtOAC to elute the required lactone. The title compound was obtained as a colourless viscous oil as a 1:1 mixture of diastereomers which solidified on standing at 5° C., $R_f$ 0.3 in EtOAc on silica plates; $^1$H NMR (360 MHz, $CDCl_3$) 1.36 and 1.37 (3H, each d, J=7Hz, $CH_3$), 1.57–1.66 (1H, m), 1.93–1.99 (1H, m), 2.19–2.25 (1H, m), 2.60–2.80 (3H, m), 2.98–3.22 (3H, m), 4.17–4.25 (1H, m, CH-O), 4.37–4.44 (1H, m, CH-O) and 7.19–7.35 (5H, m, $C_6H_5$)

Treatment of this 1:1 mixture of diastereomers with $Et_2O$ afforded the more crystalline isomer (3aS, 7aR)-2-(1R-phenethyl)-4-oxo-1,2,3,6,7,7a-hexahydropyrano[3,4-c]pyrrole (5a) as a colourless crystalline solid m.p. 82°–83° C. (Found: C, 73.54; H, 7.82; N, 5.71. $C_{15}H_{19}NO_2$ requires C, 73.44; H, 7.81; N, 5.71%); GC retention time of 35.4 min on a BP1 capillary column, 140° C. for 1 min, 140°–190° C. (2 C/min), 190° C. for 12 min; IR $_{max}$ (nujol) 1720 cm$^{-1}$ (C=O); [α] $^{24°}$ C. +28.4° (C=0.5, $CH_2Cl_2$); $^1$H NMR (360 MHz, $CDCl_3$) 1.36 (3H, d, J=7Hz, $CH_3$), 1.58–1.68 and 1.93–2.01 (2H, m, $CH_2CH_2O$), 2.23 (1H, dd, J=5,9Hz, CH—C=O), 2.61–2.70 (1H, m, $CH$CH$_2CH_2O$); 2.71–2.82 and 2.99–3.10 (4H, m, 2×$CH_2$N), 3.17 (1H, q, J=7Hz, $CH$CH$_3$), 4.20 (1H, ddd, J=2.5, 9, 11 Hz, 0.5 $CH_2O$) and 40 (1H, ddd, J=3, 6, 11Hz, 0.5$CH_2O$).

(3S,4R) Ethyl 1-((1R)-phenethyl)-1-azabicyclo-[2.2.1]heptane-3-carboxylate bromide (6)

The aminolactone (5, 108 g, 0.45 mol, 1:1 mixture of diastereomers) was dissolved in absolute EtOH (1 l) and HBr gas bubbled through the solution until saturated (~3¼h) during which time the reaction mixture warmed to reflux temperature. After saturation, the mixture was held at reflux for 2 h, cooled to room temperature and evaporated in vacuo. The residue, cooled in an ice bath, as treated with saturated $Na_2CO_3$ solution (320 ml) and the resulting mixture extracted with $CHCl_3$ (5×700 ml). The combined organic extracts were dried ($Na_2SO_4$) and evaporated in vacuo to give a viscous pale yellow gum (165 g). This gum was dissolved in IMS (70 ml), EtOAc (630 ml) was added and the mixture aged at 5° C. for 2 h. The colourless solid which had precipitated was filtered off, washed with cold acetone (200 ml) and dried (55.0 g). This solid was triturated with refluxing acetone (500 ml) for 0.5 h, cooled and again filtered to give the title compound as a colourless solid, m.p. 160°–162° C.; (Found: C, 56.80; H, 6.80; N, 3.93; Br, 22.13. $C_{17}H_{24}NO_2Br.0.25H_2O$ requires C, 56.91; H, 6.88; N, 3.90; Br, 22.27%); HPLC: $R_t$ 31.8 min (99%) on a Spherisorb phenyl+Spherisorb ODS1 column system (two columns in series) using 45% MeCN in 50mM $KH_2PO_4$, 0.2% TEA, 10 mM sodium pentane sulphonate, pH to 7.0 using $H_3PO_4$, flow rate of 1 ml/min, oven temperature=50° C.; [α]$^{24°}$ C. +21.2° (C=0.5, MeOH); $^1$H NMR (360 MHz, $CDCl_3$) 1.27 (3H, t, J=7Hz, $CH_2CH_3$), 1.68–1.80 (1H, m, 5-CH), 1.84 (3H, d, J=7Hz, CH$CH_3$), 1.94–2.06 (1H, 5-CH), 3.05–3.18 (3H, m, 4-CH, 6-CH 7-CH) 3.60–3.72 (2H m, 2-CH 6-CH), 3.92–3.97 (1H, m, 3-CH), 4.12–4.27 (2H, m, prochiral $CH_2CH_3$), 4.79 (1H, ddd, J=4, 11Hz, 2-CH), 4.88 (1H, d, J=8Hz, 7-CH), 5.88 (1H, q, J=7Hz, $CH$CH$_3$), 7.44–7.47 (3H, m) and 7.66–7.69 (2H, m, $C_6H_5$).

(3S,4R)-Ethyl-1-azabicyclo2.2.11 heptane-3-carboxylate hydrogen oxalate (7)

A mixture of the quaternary salt (6. 89.5 g, 0.25 mol), 10% Pd on C (9.0 g, wetted with $H_2O$ (25 ml)) and EtOH (800 ml) was hydrogenated at 50 psi for 48 h. The reaction mixture was filtered through HYFLO and evaporated to dryness. The residue was dissolved in $H_2O$ (100 ml), cooled in an ice bath and basified with solid $Na_2CO_3$ (31 g, 0.29 mol). The free base was extracted into $CH_2Cl_2$ (5×200 ml) and the combined organics dried ($Na_2SO_4$) and evaporated in vacuo to give a colourless oil (41.2 g). This oil in iPA (200 ml) was treated with a solution of oxalic acid (22.5 g, 0.25 mol) in iPA (200 ml). The mixture was warmed on a steam bath, cooled to room temperature and then aged for 4 h. The salt was collected by filtration and recrystallised from iPA (380 ml) to give 7 as a colourless crystalline solid (51.8 g, 80%), m.p. 126° C.; (Found: C, 50.87; H, 6.53; N, 5.38. $C_9H_{15}NO_2.C_2H_2O_4$ requires C, 50.96; H, 6.61; N, 5.40%); $R_f$ 0.14 in $CH_2Cl_2$/MeOH (9:1) on silica plates; [α]$^{25°}$C. +32.0° (c=0.5, MeOH); $^1$H NMR (360 MHz, $D_2O$) 1.28 (3H, t, J=7Hz, $CH_2CH_3$), 1.69–1.78 (1H, m, 5-CH), 2.04–2.14 (1H, m, 5-CH), 3.24–3.38 and 3.43–3.61 (8H, m, 2-$CH_2$, 3-CH, 4-CH, 6-$CH_2$ and 7-$CH_2$) and 4.20–4.29 (2H, m, prochiral $CH_2CH_3$).

Cyclopropyl carboxamide oxime

A slurry of hydroxylamine hydrochloride (46.8 g, 0.673 mol) in MeOH (350 ml) was added to a stirred solution of sodium (16.32 g, 0.709 mol) in MeOH (300 ml) under a nitrogen atmosphere. After 10 min, cyclopropyl cyanide (50.0 g, 0.745 mol) was added dropwise and the mixture was stirred at room temperature for 3 days. The mixture was filtered, and the material isolated after removal of the methanol was distilled twice under vacuum to give the required amide oxime (43.2 g, 58%) as a viscous oil which solidified on storage at 5° C.; b.p. 110° C. (1.7 mmHg); (Found: C, 48.53; H, 8.19; N, 27.28. $C_4H_8N_2O$ requires C, 47.99; H, 8.05; N, 27.98%). $^1$H NMR (360 MHz $d_6$DMSO) 0.51–0.66 (4H, m, $2 \times CH_2$), 1.28–1.36 (1H, m, CH), 5.19 (2H, s, $NH_2$) and 8.70 (1H, m, NOH).

The enantiomer of formula (A) or (B) may alternatively be prepared by the method of or a method analogous to that described in British patent applications Nos. 8911081 and 8923014, which are each incorporated herein by reference.

Alternatively, compound (I) may be prepared according to the following scheme 2 or a method analogous thereto. For example, $R^1$ in formulae (9) and (10) may be any labile leaving group such as mesylate (shown) or lower alkanoate such as acetate; and R in formula (10) may be any salt produced during the deblocking step ((9) to (10)) such as the trifluoroacetate (shown) or hydrogen halide such as HCl or HBr salts.

Also, the blocking group —$COOC(Me)_3$ may be any secondary amine blocking group such as, alternatively, benzyloxycarbonyl. The leaving group (mesylate) in formula (3) may be any as mentioned in respect of $R^1$ above or p-toluenesulphonate. The ethyl ester of formula (6) may be instead any lower alkyl or benzyl ester, for example.

SCHEME 2

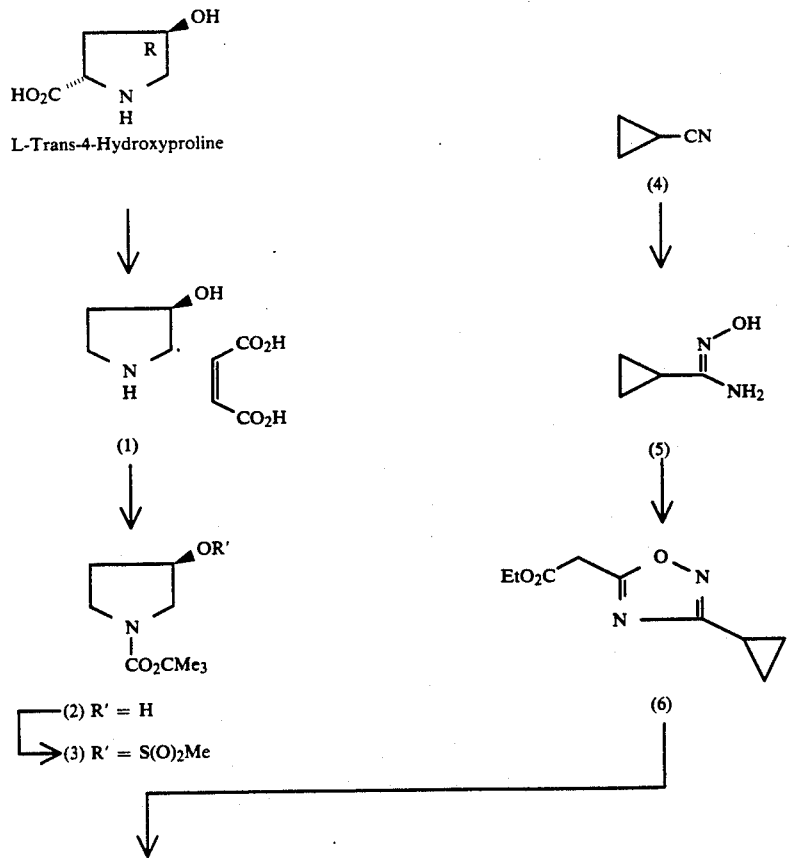

SCHEME 2 -continued

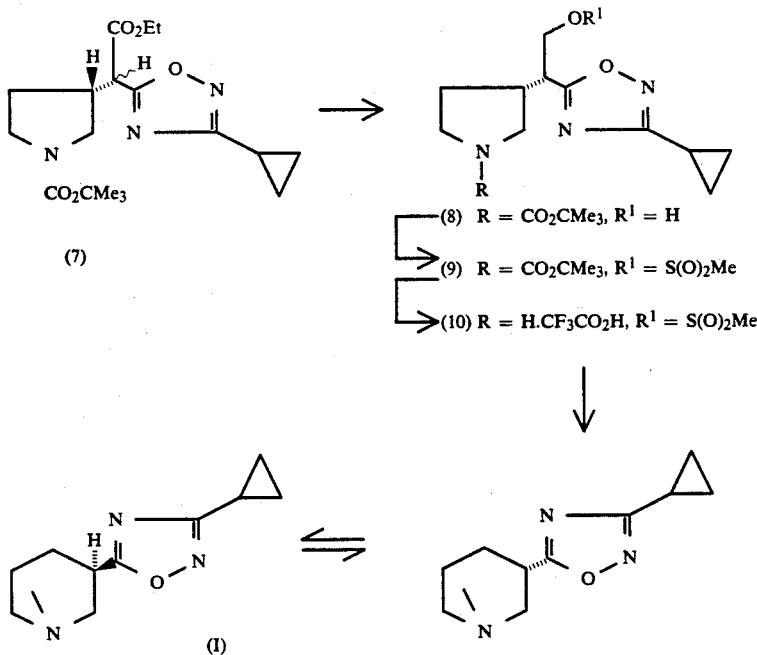

(8) R = CO₂CMe₃, R¹ = H
(9) R = CO₂CMe₃, R¹ = S(O)₂Me
(10) R = H.CF₃CO₂H, R¹ = S(O)₂Me

Also included within the scope of the present invention are salts of (3R, 4R)-3-(3-cyclopropyl-1,2,4-oxadiazol-5-yl)-1-azabicyclo[2.2.1]heptane. It will be appreciated that salts of the compound for use in medicine will be non-toxic pharmaceutically acceptable salts. Other salts may, however, be useful for the preparation of the base or its non-toxic pharmaceutically acceptable salts. Acid addition salts, for example, may be formed by mixing a solution of the compound with a solution of a pharmaceutically acceptable non-toxic acid such as hydrochloric acid, fumaric acid, maleic acid, succinic acid, acetic acid, citric acid, tartaric acid, p-toluene sulphonic acid, carbonic acid or phosphoric acid. Preferred are the hydrochloride, hydrogen maleate, hydrogen tartrate and tosylate salts.

This invention also provides a method of treating Alzheimer's disease, senile dementia of the Alzheimer type, Huntington's chorea, tardive dyskinesia, hyperkinesia, mania or Tourette syndrome by the administration to a patient in need of such treatment of a pharmacologically effective amount of compound (I).

It may, where appropriate, be advantageous, in order to reduce unwanted peripherally mediated side-effects, to incorporate into the composition a peripherally acting cholinergic antagonist (or anti-muscarinic agent). Thus compound (I) may be administered together with a peripheral cholinergic antagonist such as N-methyl-scopolamine, N-methylatropine, propantheline, methantheline or glxcopyrrolate.

Compound (I) can be administered orally, parenterally or rectally at a daily dose of about 0.001 to 10 mg/kg of body weight, preferably about 0.01 to 1 mg/kg, and may be administered on a regimen of 1–4 times a day. When a cholinergic antagonist is administered, it is incorporated at its conventional dose.

This invention also provides a -pharmaceutical composition comprising compound (I) and a pharmaceutically acceptable carrier therefor.

The pharmaceutical formulations of this invention preferably are in unit dosage form such as tablets, pills, capsules, powders, granules, sterile parenteral solutions or suspensions, or suppositories, which forms are for oral, parenteral or rectal administration. For preparing solid compositions such as tablets, the principal active ingredient is mixed with a pharmaceutical carrier, e.g. conventional tabletting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of compound (I). When referring to these preformulation compositions as homogeneous, it is meant that the active ingredient is dispersed evenly throughout the composition so that the composition may be readily subdivided into equally effective unit dosage forms such as tablets, pills or capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids or mixtures of polymeric acids with such materials as shellac, cetyl alcohol and cellulose acetate.

The liquid forms in which the novel compositions of the present invention may be incorporated for administration orally or by injection include aqueous solutions, suitably flavoured syrups and flavoured emulsions with edible oils such as cottonseed oil, sesame oil, coconut oil and peanut oil, as well as elixirs and similar pharmaceutical vehicles. Suitable dispersing or suspending agents for aqueous suspension include synthetic and natural gums such as tragacanth, acacia, alginate, dextran, sodium carboxymethylcellulose, methylcellulose, polyvinylpyrrolidone and gelatin.

The present invention therefore further provides a process for preparing a pharmaceutical composition according to the invention which process comprises bringing compound (I) into association with a carrier therefor, such as by mixing. The present invention will now be illustrated by the following examples.

EXAMPLE 1

(3R,4R)-3-(3-Cyclopropyl-1,2,4-oxadiazol-5-yl)-1-azabicyclo [2.2.1]heptane [The numbers in the titles refer to those in Scheme 2]

A. Preparation of (3R)-3-Hydroxypyrrolidine (1) Hydrogen Maleate

A 20 liter flange flask equipped with mechanical stirrer, thermometer, nitrogen inlet and condenser, was charged with trans L-hydroxyproline (Degussa, 1.00 kg, 7.63 Mol), cyclohexanol (Aldrich 30818, 5.0 l) and 2-cyclohexen-1-one (Lancaster, 100 ml). The slurry was stirred and heated at vigorous reflux (~155° C.) until complete solution was observed (5.5 h). The clear red solution was cooled to 25° C. and maleic acid (885 g, 7.63 Mol) added in portions over 30 min. The reaction temperature was maintained at 30°–35° C. during addition. On complete addition, crystallisation occurred and the slurry was aged at 25° C. for 30 min. Ethyl acetate (10.0 l) was added dropwise over 1 h and the resultant slurry allowed to age at room temperature for 2 h. The slurry was filtered, the cake washed with ethyl acetate/cyclohexanol (2/1, 3.0 l), ethyl acetate (3.0 l), and dried in vacuo at 20° C. overnight.

B. Preparation of (3R)-N-(t-Butoxycarbonyl)-3-hydroxypyrrolidine (2)

A 10 gallon glass-lined vessel was charged with water (29 l) and sodium bicarbonate (7.42 kg, 88.3 Mol). To the resultant stirred slurry, at 20° C., was added a solution of (3R)-3-hydroxypyrrolidine hydrogen maleate (1) (3.60 kg, 17.7 Mol) in water (10.8 l), over 15 min (effervescence). On complete addition, di-tertbutyldicarbonate (Fluka, 4.64 kg, 21.3 Mol) was added in one portion (no exotherm noted). The slurry was vigorously stirred over the weekend (i.e. total ~65 h).

Ethyl acetate (10 l) was added and the mixture filtered to remove suspended solids. The aqueous layer was separated and re-extracted with ethyl acetate (10 l). The combined organics were dried (Na$_2$SO$_4$) and evaporated under reduced pressure to give a colourless oil.

C. Preparation of (3R)-N-(t-Butoxycarbonyl)-3-methanesulphonyloxypyrrolidine (3)

A dry 10 gallon glass-lined vessel was charged with the alcohol (2) (3.39 kg d.b., 18.1 Mol) and ethyl acetate (50 l) under nitrogen. The solution was cooled to −5° C. and triethylamine (Lancaster B/N 076337, 5.1 l) was added in one portion. Methanesulphonyl chloride (Lancaster B/N 79561, 1.68 l, 21.7 Mol) was added dropwise over 1 h, maintaining the reaction temperature at −5-2° C. On complete addition, the slurry was aged at −5° C. for 30 min.

Water (20 l) was added over 10 min and the phases well mixed. The aqueous layer was separated and the organics washed with 1 M aqueous hydrochloric acid (10 l), saturated sodium bicarbonate (10 l) and dried (Na$_2$SO$_4$). Solvent evaporation gave the product as a pale yellow oil.

D. Preparation of Cyclopropylcarboxamide Oxime (5)

A 20 gallon glass-lined vessel was charged with methanol (32 l), hydroxylamine hydrochloride (Lancaster, 3.88 kg, 55.8 Mol) and cyclopropyl cyanide (Fluka BN 533321, 4.50 kg, 5.01, 67.1 Mol) under a nitrogen atmosphere. A solution of potassium carbonate (7.72 kg, 55.9 Mol) in water (28 l) was added dropwise with stirring over 20 min. Effervescence and a slight exotherm (15° to 20° C.) was noted. After complete addition the stirred mixture was warmed to 70° C.±2° C., to maintain a slight reflux, for 18 h. The reaction mixture was cooled to 55 C and the solvents distilled under reduced pressure to a residual volume of ~20 l. The residue was transferred to a 20 l Buchi apparatus and the remaining solvents removed. The oily-solid residue was swished in THF (10 l) and filtered. The cake was washed with THF (10 l) and the filtrates dried (Na$_2$SO$_4$). Evaporation of solvents gave a colourless oil which solidified on standing at ~5° C.

E. Preparation of Ethyl-2-(3-cyclopropyl-1.2.4-oxadiazol-5-yl)acetate (6)

A 20 gallon glass-lined vessel was charged with cyclopropylcarboxamide oxime (5) (5.39 kg, 53.9 Mol), toluene (Shell Chem, 324, 54.0 l) and diethylmalonate (Lancaster B/N 52068785, 24:5 kg, 160 Mol) under nitrogen at room temperature. The stirred reaction mixture was heated at gentle reflux for 21 h. The ethanol/water produced during the reaction was periodically drawn off to maintain a high reflux temperature (i.e 105°–110° C.). The reaction mixture was cooled to room temperature, washed with 25% saturated brine (3×5 l) and the toluene removed under reduced pressure. The residue was distilled using a small fractionating column to give: a) recovered diethylmalonate b.p. 60°–70° C. at 2 mbar; and b) oxadiazole-ester (6) b.p. 90°–120° C., at ~2 mbar.

F. Preparation of (2S,3'R) and (2R,3'R) Ethyl-2-(3-cyclopropyl-1,2,4-oxadiazol-5-yl)-2-N-(t-butoxycarbonyl)pyrrolidin-3-yl1acetate (7)

A 20 liter flange flask fitted with mechanical stirrer, nitrogen inlet and addition funnel was charged with the ester (6) (6.24 kg, 31.8 Mol) and mesylate (3) (4.22 kg, 15.9 Mol). Diazabicyclo[5.4.0]undec-7-ene (Fluka B/N 538856, 4.60 kg, 30.2 Mol) was added dropwise to the stirred mixture, at 20° C., over 20 min (an exotherm to 45° C. was noted). The resultant solution was heated (temperature controlled water bath) to 54±1° C. for 30 hours. The reaction mixture was cooled to 20° C. and partitioned between ethyl acetate (12.5 l) and 1N hydrochloric acid (8 l). The organic layer was separated and washed with 1M hydrochloric acid (4 l), 50% saturated brine solution (2×5 l) and dried Na$_2$SO$_4$. Evaporation of solvents under reduced pressure gave a red oil. The crude oil was passed down a short path distillation apparatus at 130° C. and 0.4–0.7 mmHg to remove the excess ester (6) and pyrrolidine (3). A red, viscous, residual oil was obtained and used 'as is' in the following reduction step.

G. Preparation of (2S,3'R) and (2R,3'R) 2-(3-Cyclopropyl-1,2,4-oxadiazol-5-yl)-2-N-(t-butoxycarbonyl)-pyrrolidin-3-yl]ethanol (8)

To a stirred solution of alkylated ester (7) (6.20 kg, 15.99 Mol) in dry THF (Fisons B/N 14288129, 18.6 l) at −5° C., under nitrogen, was added sodium borohydride (Lancaster, 2.57 kg, 67.9 Mol) portion wise maintaining the reaction temperature ~ −5° C. Methanol (13.8 l) was added dropwise over 1 h maintaining reaction temperature −5°-0° C. On complete addition, the reaction was stirred at −5° C. for a further 3 h. TLC (Ether/Silica) showed complete consumption of starting material. The reaction mixture was cooled to −20° C. (to avoid over-reduction) and added, via a cannula, to a stirred mixture of ethyl acetate (30 l) and 2N hydrochloric acid (146 l) at −10° to −5° C. The quench temperature was maintained by addition of solid carbon dioxide. On complete addition, the stirred mixture was aged for 15 minutes at <0° C. and then allowed to settle. The aqueous layer was separated, and re-extracted with ethyl acetate (5×15 l). The organics were combined, washed with 2N hydrochloric acid (13 l), saturated brine (3×13 l) and dried (Na$_2$SO$_4$). The solvent was evaporated to give the alcohols (8) as a dark oil.

H. Preparation of Methanesulphonate Esters (9)

A 20 gallon glass-lined vessel was charged with alcohol (8) (4.6 kg, 12.2 Mol) and ethyl acetate (Alcohols Ltd., B/N 21189, 46 l). The solution was cooled to −20° C. using internal, liquid nitrogen cooling and triethylamine (Lancaster, O/N 076337, 3.97 l, 28.4 Mol) added over 10 min. Methanesulphonylchloride (Lancaster, B/N 91466-00-474, 1.32 l, 17.1 Mol) was added slowly over 0.5 h maintaining the reaction temperature between −20° and −15° C. On complete addition the reaction was aged at −20° C. for 0.75 h. 2M Hydrochloric acid (14.4 l) was added dropwise, allowing the reaction temperature to rise to −10° C. The lower aqueous layer was removed and reextracted with ethyl acetate (3×3.0 l). The combined organics were washed with saturated brine solution (4×6.4 l), concentrated to ~10 l, filtered and the remaining solvent evaporated (Buchi) to leave a dark oil (unstable to GC/MS).

I. Preparation of (3S, 4R) and (3R, 4R)-3-(3-Cyclopropyl-1,2,4-oxadiazol-5-yl)-1-azabicyclo-[2.2.1]heptane To a solution of the methanesulphonate esters (9) (5.90 kg, 14.7 Mol) in t-butanol (Fisons B/N 12, 15, 52 and Aldrich B/N 28758, 3.0 l) at room temperature was added trifluoroacetic acid (Fluorochem B/N F07160, Aldrich B/N 33525, 12.0 l) dropwise over 1 h. The reaction temperature was maintained between 20°–25° C. during the addition. After a further 1 h age period, TLC (Ether/Silica) showed no starting material remaining. The reaction mixture was diluted with t-butanol (Aldrich B/N 28758, 24.0 l) and 10% aqueous sodium carbonate (~80 l) added to adjust the pH to 7.5. The reaction mixture was heated to 40° C. and the pH maintained constant for 1.5 h by the addition of aqueous carbonate. The pH was raised to 8.5 for 1.5 h and finally increased to 9.5 whereupon the product was extracted into toluene (20.0 l). The aqueous layer was separated and extracted with toluene (4×10 l). The organics were combined and dried (Na$_2$SO$_4$). Evaporation of solvent gave a dark oil. The crude product was purified by chromatography on silica gel (Merck Kieselgel 60, ART 7734, B/N TA 534034 50 kg) using first ethyl acetate/methanol (5/1) then methanol to elute the endo isomer. Pure exo isomer free base along with an endo/exo mixture was obtained. To a solution of the free base exo/endo mixture (10.0 g) in IMS (20 ml) was added a solution of potassium t-butoxide (1.0 g) in IMS (30 ml). The solution was heated at gentle reflux for 30 min. The epimerisation was generally complete after this period. The reaction mixture was extracted with ethyl acetate (2×10 ml), the organics combined and dried (Na$_2$SO$_4$). The solvent was evaporated to residue and partitioned between water (15 ml) and ethyl acetate (15 ml). The aqueous layer was evaporated to give an oil, 9.8 g, 98% recovery, ratio of exo:endo (76:24).

EXAMPLE 2

Preparation of (3R, 4R)-3-(3-Cyclopropyl-1,2,4-oxadiazol-5-yl)-1-azabicyclo[2.2.1]heptane p-toluenesulphonate A solution of p-toluenesulphonic acid monohydrate (109 g, 0.57 Mol) in ethyl acetate (500 ml) was dried by azeotropic distillation (170 ml removed). To the resultant cooled solution was added isopropylalcohol (120 ml). A pre-filtered solution of epimerised free base (exo/endo; 74/26, 118 g, 0.57 Mol) in ethyl acetate (260 ml) and IPA (116 ml) was added at room temperature over 10 min (exotherm to 40° C.). The solution was seeded with pure pTSA salt of the base (~20 mg) and the slurry allowed to age at room temperature for 2 h. The slurry was chilled at 0.5° C. for 1 h, filtered and the cake washed with ethyl acetate (200 ml). The white crystalline solid was dried in vacuo at room temperature, swished in ethyl acetate (10 mlg$^{-1}$) at reflux for 2 h, cooled to room temperature (1 h), filtered and the cake washed with ethyl acetate (100 ml). The white crystalline solid was dried in vacuo to give pTSA salt m.p. 130°–131° C. (propan-2-ol/ethyl acetate).

EXAMPLE 3

Preparation of (3R, 4R)-3-(3-Cyclopropyl-1,2,4-oxadiazol-5-yl)-1-azabicyclo[2.2.1]heptane hydrogen maleate Swished pTSA salt (prepared as in Example 2) (>99.5% by GC, 204 g) was partitioned between ethyl acetate (200 ml) and saturated sodium carbonate (1 l). The aqueous layer was separated and extracted with ethyl acetate (5×100 ml). The organics were combined, dried (Na$_2$SO$_4$) and evaporated to give a pale yellow oil which solidified on standing.

To a pre-filtered solution of maleic acid (58.9 g, 0.50 Mol) in isopropyl alcohol (188 ml) at 30° C. was added a pre-filtered solution of the free base (104 g, 0.50 Mol) in isopropyl alcohol (99 ml) over 10 min. The slurry was cooled to 20° C. and ethyl acetate (412 ml) added over 15 min and the mixture aged for 1 h. The slurry was cooled to 0°–5° C., held for 1 h and filtered. The cake was washed with ethyl acetate (300 ml) and dried in vacuo at room temperature overnight to give the hydrogen maleate salt (analytical data consistent with that given in Example 6).

EXAMPLE 4

(3R,4R)-3-(3-cyclopropyl-1,2,4-oxadiazol-5-yl)-1-azabicyclo[2.2.1]heptane (2R,3R)hydrogen tartrate A solution of the free base (184 mg, 0.9 mmol) in iPA (3 ml) was added to a hot solution of L-(+)-(2R,3R)-tartaric acid (135 mg, 0.9 mmol) in iPA (3 ml). On cooling, a crystalline precipitate was produced which was recovered and recrystallised from ethanol (4 ml) to give a colourless crystalline solid.

mp 124°-125° C. (ethanol)

Found:C,50.66;H,5.97;N,11.76 $C_{15}H_{21}N_3O_7$ requires C,50.70;H,5.96;N,11.83%

EXAMPLE 5

(3R,4R)-3-(3-Cyclopropyl-1,2,4-oxadiazol-5-yl)-1-azabicyclo[2.2.1]heptane. Hydrochloride (3S,4R)-Ethyl-1-azabicyclo[2.2.1]heptane-3-carboxylate hydrogen oxalate (61.7 g, 0.24 mol) in $H_2O$ (200 ml) was cooled in an ice bath, $Na_2CO_3$ (38 g, 0.36 mol) added and the mixture extracted with $CH_2Cl_2$ (5×250 mL). The combined organics were dried ($Na_2SO_4$) and evaporated to give the free base as a colourless oil (38.2 g, 94%). To a stirred solution of cyclopropyl carboxamide oxime (22.6 g, 0.226 mol) in dry THF (500 mL) was added 4A molecular sieves (40 g). After 0.5 h, NaH (9.9 g of a 55% dispersion in oil, 0.226 mol) was added under a nitrogen atmosphere in portions over 40 min. After addition was complete, the mixture was heated at 50° C. (oil bath temperature) for 1 h. A solution of the ester free base (19.1 g, 0.113 mol, obtained above) in dry THF (200 mL) was added and the mixture heated under reflux for 3 h. After cooling, $H_2O$ (100 mL) was added and the mixture stirred for a further 15 min before filtering. The filtrate was evaporated in vacuo to remove most of the THF and the crude product was extracted into $CH_2Cl_2$ (5 ×250 mL). The combined organics were dried ($Na_2SO_4$) then evaporated to give a yellow oil (25.1 g) which was combined with a similar quantity from an identical reaction (total 49.3 g). Column chromatography on neutral alumina (ICN Neutral Alumina, Grade 3; 2.2 Kg) using $CH_2Cl_2$/MeOH (100:1) gave pure exo-(3R,4R) product as a pale yellow oil (18.05 g, $R_t$ 10.12 min (>99%), BP10 Capillary GC column, 170° C. isothermal). Mixed fractions were also obtained (~1:1 exo/enco, 13.25 g) and this material was re-equilibrated under thermodynamic conditions using NaOMe (4.8 g; 1.5 equivalents) in MeOH (100 mL) at reflux for 2 h. The mixture was evaporated and partitioned between $H_2O$ (40 mL) and $CH_2Cl_2$ (100 mL). The organic layer was separated and the aqueous re-extracted with $CH_2Cl_2$ (2×100 mL). The combined organic extracts were dried and evaporated to give a pale yellow oil (13.0 g; ~5:1, exo/endo) to afford a further supply of pure exo isomer (7.8 g) after column chromatography on neutral alumina (total yield, 25.85 g). This material in $Et_2O$ (180 mL) containing iPA (18 mL) was filtered and cooled (ice bath) and then treated with saturated etherial HCl. After ageing for 0.5 h at 5° C., the crude salt was collected (24.4 g) and recrystallised twice from iPA (60 mL each time) to afford the title compound as a white crystalline solid (18.0 g; 31%), m.p. 169°-170° C.; (Found: C, 54.65; H, 6.67; N, 17.32; Cl, 14.76. $C_{11}H_{15}N_3O$.HCl requires C, 54.66; H, 6.67; N, 17.38; Cl, 14.67%; $R_f$ 0.62 in $CH_2Cl_2$/MeOH (50:1) on alumina plates; $[\alpha]^{22}_D$·C·−0.30° (c=1.0, MeOH); $[\alpha]^{22}_D$·C·−17.4° (c=1.0, $CH_2Cl_2$); HPLC, chemical purity: $R_t$ 6.56 min (99.9%) at λ=210 nm on a Spherisorb ODS2 column (250×4.6 mm), 10% MeCN in 50 mM $KH_2PO_4$, 0.2% TEA, pH=2.5 with $H_3PO_4$, flow rate 1 mL/min; HPLC, enantiomeric purity: $R_t$ 7.06 min (> 99%) at λ=205 nm on an Enantiopac column, 5 mM $K_2HPO_4$, 0.5 mM t-butyldihydrogen ammonium phosphate, pH=7.5 with $H_3PO_4$, flow rate 0.3 mL/min; MS, m/z 205 M+ of free base; IR $v_{max}$ (nujol) 2800-2400 (NH+), 1580 cm$^{-1}$ (C=N); $^1$H NMR (360 MHz, $D_2O$) δ0.95-1.02 (2H, m, cyclopropyl-$CH_2$), 1.11-1.21 (2H, m, cyclopropyl-$CH_2$), 1.96-2.05 (1H, m, 5-CH). 2.08-2.16 (1H, m, cyclopropyl-CH), 2.23-2.33 (1H, m, 5-CH), 3.30-3.46 (4H, m, 4-CH, 6-CH, 7-$CH_2$), 3.50-3.60 (1H, m, 6-CH) and 3.71-3.87 (3H, m, 2-$CH_2$ and 3-CH).

EXAMPLE 6

(3R,4R)-3-(3-Cyclopropyl-1,2,4-oxadiazol-5-yl)-1-azabicyclo[2.2.1]heptane Hydrogen Maleate (alternative preparation)

A solution of anhydrous maleic acid (4.30 g, 0.037 mol) in methanol (12 mL) and diethyl ether (4 mL) was added to a filtered solution of (3R,4R)-3-(3-cyclopropyl-1,2,4-oxadiazol-5-yl)-1-azabicyclo[2.2.1]heptane free base (7.60 g, 0.037 mol) in methanol (6 mL) and diethyl ether (6 mL). After ageing at 5° C. for 16 hours the hydrogen maleate salt (9.10 g) was collected, mp 126° C. (propan-2-ol). $[\alpha]^{21}_D$·C·−7.0° (c=1.0, $CH_2Cl_2$). (Found: C, 56.06; H, 5.97; N, 13.04. $C_{11}H_{15}N_3O$. $C_4H_4O_4$ requires C, 56.07; H, 5.96; N, 13,08%).

EXAMPLE 7

(3R,4R)-3-(3-Cyclopropyl-1,2,4-oxadiazol-5-yl)-1-azabicyclo[2.2.1[heptane Hydrogen Fumarate A solution of anhydrous fumaric acid (0.142 g, 1.2 mmol) in methanol (2 mL) was added to a solution of (3R,4R)-3-(3-cyclopropyl-1,2,4-oxadiazol-5-yl)-1-azabicyclo[2.2.1]heptane free base (0.25 g, 1.2 mmol) in diethyl ether (2 mL) containing methanol (0.5 mL). The hydrogen fumarate salt obtained (0.085 g) had mp (120°-121° C.

EXAMPLE 8

(3R,4R)-3-(3-Cyclopropyl-1,2,4-oxadiazol-5-yl)-1-azabicyclo[2.2.1]heptane Hydrochloride Sodium hydride (0.105 g of a 55% dispersion in oil) was added to a stirred mixture of cyclopropyl carboxamide oxime (0.24 g, 2.4 mmol) and 4 A molecular sieves (0.5 g) in anhydrous tetrahydrofuran (10 mL) under a nitrogen atmosphere. After heating under reflux for 45 minutes the mixture was cooled then a solution of (3R,4R)-methyl-1-azabicyclo[2.2.1]heptane-3-carboxylate (0.156 g, 1.0 mmol, obtained from the (+) hydrogen oxalate salt) in anhydrous tetrahydrofuran (5 mL) was added and the mixture heated under reflux for 2.5 hours with stirring. The reaction mixture was worked up as described in Example 1 to afford the title compound free base (0.082 g, 40%) as an oil. The hydrochloride salt had mp 167°-169° C. (propan-2-ol/diethyl ether). $[\alpha]^{22}_D$·C·−16.2° (c=0.5, $CH_2Cl_2$). (Found: C, 54.42; H, 6.66; N, 17.11. $C_{11}H_{15}N_3O$.HCl requires C,54.66; H, 6.67; N, 17.38%).

EXAMPLE 9

Tablet Preparation

Tablets containing 1.0, 2.0, 25.0, 26.0, 50.0 and 100.0 mg, respectively, of (3R,4R)-3-(3-Cyclopropyl-1,2,4-oxadiazol-5-yl)-1-azabicyclo[2.2.1]heptane are prepared as illustrated below.

| TABLE FOR DOSES CONTAINING FROM 1-25 MG OF THE ACTIVE COMPOUND | | | |
|---|---|---|---|
| | Amount-mg. | | |
| Active Compound | 1.0 | 2.0 | 25.0 |
| Microcrystalline cellulose | 49.25 | 48.75 | 37.25 |
| Modified food corn starch | 49.25 | 48.75 | 37.25 |
| Magnesium stearate | 0.50 | 0.50 | 0.50 |

| TABLE FOR DOSES CONTAINING FROM 26-100 MG OF THE ACTIVE COMPOUND | | | |
|---|---|---|---|
| | Amount-mg. | | |
| Active Compound | 26.0 | 50.0 | 100.0 |
| Microcrystalline cellulose | 52.0 | 100.0 | 200.0 |
| Modified food corn starch | 2.21 | 4.25 | 8.5 |
| Magnesium stearate | 0.39 | 0.75 | 1.5 |

All of the active compound, lactose, and a portion of the corn starch are mixed and granulated to 10% corn starch paste. The resulting granulation is sieved, dried and blended with the remainder of the corn starch and the magnesium stearate. The resulting granulation is then compressed into tablets containing 1.0 mg, 2.0 mg, 25.0 mg, 50.0 mg, and 100 mg of active ingredient per tablet.

BIOLOGICAL DATA

A. By the method disclosed in Br. J. Pharmacol. (1988), 93, 437-445 were determined the NMS/OXO-M data for the compound (I): [$^3$H]NMS $K_{app}$=0.025 μM; [$^3$H]OXO-M $K_{app}$=0.0017 μM; ratio NMS/OXO-M=15; ($K_{app}$=corrected dissociation constant allowing for ligand occupancy).

B. By the methods disclosed in J. Med. Chem. (1987), 30, 969-975 was determined the functional selectivity of compound (I):

| Preparation | Receptor | pEC$_{50}$ | Rel. Max. | pA2 |
|---|---|---|---|---|
| Rat superior cervical ganglion | M-1 | 7.2 ± 0.2 (5) | 0.55 ± 0.1 (5) | |
| Guinea-pig atrium | M-2 | | 0 | 8.00 (7.80-8.20; 10) |
| Guinea-pig myenteric plexus/ longitudinal muscle strip | M-3 | | 0 | 8.15 (7.90-8.40; 12) | pEC$_{50}$ and relative maximum are mean ± S.D. (n)
pA$_2$ (95% confidence limits, n). None of the slopes of the Arunlakshana-Schild plots differ significantly from unity.

What we claim is:
1. A compound, (3R,4R)-3-(3-cyclopropyl-1,2,4-oxadiazol-5-yl)-1-azabicyclo[2.2.1]heptane or salt thereof.
2. The compound according to claim 1, wherein said salt is selected from the group consisting of hydrochloride, hydrogen maleate, hydrogen tartrate and tosylate.
3. A pharmaceutical composition comprising an effective amount of (3R,4R)-3-(3-cyclopropyl-1,2,4-oxadiazol-5-yl)-1-azabicyclo[2.2.1] heptane or a pharmaceutically acceptable salt thereof in association with a pharmaceutically acceptable carrier.
4. A method for the treatment of neurological and mental disorders, wherein said method comprises the administration to a patient in need thereof of a pharmacologically effective amount of a compound according to claim 1.
5. The method according to claim 4, wherein the disorder is dementia.

* * * * *